United States Patent [19]

Eichhoefer

[11] Patent Number: 4,891,222

[45] Date of Patent: Jan. 2, 1990

[54] PINE OIL FIRE ANT INSECTICIDE

[76] Inventor: Gerald W. Eichhoefer, 809 Magnolia Ct., Liberty, Mo. 64068

[21] Appl. No.: 17,739

[22] Filed: Feb. 24, 1987

[51] Int. Cl.$^4$ ............................................. A01N 65/00
[52] U.S. Cl. ................................................... 424/196.1
[58] Field of Search ..................................... 424/196.1

[56] References Cited

FOREIGN PATENT DOCUMENTS

| 550878 | 11/1956 | Italy | 424/196.1 |
| 0908296 | 5/1980 | U.S.S.R. | 424/196.1 |
| 1464716 | 2/1977 | United Kingdom | 424/196.1 |

OTHER PUBLICATIONS

Chem. Abst. 72:20843s, 1970.
Chem. Abst. 76:55225b, 1972.

*Primary Examiner*—John W. Rollins
*Attorney, Agent, or Firm*—Peter F. Casella

[57] ABSTRACT

This invention relates to the use of mixtures of terpene alcohols and terpene hydrocarbons, such as pine oil, in combination with surface active agents of the anionic and nonionic type containing dispersing and stabilizing agents, for controlling the population of certain colonial insects, especially fire ants.

6 Claims, No Drawings

PINE OIL FIRE ANT INSECTICIDE

BACKGROUND OF THE INVENTION

There is a scurge of insects invading the United States and many other parts of the world in increasing numbers, ever since government restrictions have been placed on the use of chemicals that have been employed in controlling them. The government restrictions have been imposed in the effort to protect the environment from real or imaginary toxic effects of the chemicals employed. Among the chemicals banned or restricted in use by governments are DDT, Chlorodane, Lindane, Aldrin, Heptechlor, Dieldrin and Mirex. Mirex was employed as an effective insecticide against fire ants, however since its use has been banned in the United States, the fire ant population has been increasing so rapidly that major destruction of crops such as soybeans, potatoes, and other vegetables, has been occurring in the sun belt region of the United States where the fire ant is taking over. In addition fire ants have been known to kill young birds and even small rodents and they will feed on anything or anybody that collaspses from their multiple stings. They are a menace to people in homes, schools, work places, and even in medical facilities, to domestic animals, and especially in agriculture. Fire ants destroy lawns and forage tunnels in the ground and infest any buildings above them. One species, *Solenopsis invicta* is reported to nest in super colonies called insect megalopolises, containing 10 to 20 million ants.

PRIOR ART

The order Hymenoptera, family Formicidae includes numerous species of ants. The order Isooptera, family Termitidae includes various species of termites. Representative species of ants and termites are given in Columns 3 and 4 in U.S. Pat. No. 4,421,759 issued to R. J. Boisvenue on Dec. 20, 1983 and assigned to Eli Lilly & Company. This patent discloses and claims the use of fluoro-benzimidazoles and fluoro-benzimidazolines for controlling ants and termites, especially fire ants.

Another patent directed to the control of fire ants is U.S. Pat. No. 4,353,907 issued to J. B. Lovell on Oct. 12, 1982 and assigned to American Cyanamid Company. This patent discloses and claims the use of fluoro-aminido hydrazones and their bait formulations with edible oils, such as soybean oil, cottenseed oil, coconut oil, corn oil, olive oil, peanut oil, palm oil, tall oil, and their mixtures, for controlling fire ants.

Still another patent directed to the control of fire ants is U.S. Pat. No. 3,220,921 issued to Greenbaum and Weil on Nov. 30, 1965 and assigned to the Hooker Chemical Corporation. This patent disclosed and claims the dimer of hexachlorocycyopentadiene, also known as Mirex, with baits such as peanut butter. Mirex was found to be one of the most effective fire ant killers and was employed in solid baits such as peanut butter and ground up corn cobs because of its pronounced toxicity when ingested in the insects digestive tract, as distinguished from its contact insecticidal activity which is not so great. Although Mirex is an effective agent for killing fire ants it can not be employed in those juristrictions where it has been banned because it is toxic to the environment.

Pine oil is a naturally occuring material, which is obtained by the distillation of the cones, needles, stumps, etc. of various species of pines, which are coniferous trees. They consist principally of isomeric tertiary and cyclic terpene hydrocarbons and alcohols, with variable quantities of terpene ethers, ketones, phenols, phenolic ethers amoung other constituents, including alpha pinene.

Various patents have been issued on the use of materials originating from pine trees. For example, U.S. Pat. No. 141,512 issued to J. B. Lunbeck back in Aug. 5, 1873 discloses a composition produced by boiling one gallon of pine tar; one quart of soft soap; one-half pint of tobacco juice and one-half gallon of alkali for use in destroying insects, worms and grubs and protecting fruit and other trees. Another patent issued to G. C. Richards on Apr. 13, 1926 discloses and claims an insecticide paint made from pine tar, a thinner, sulfur and carbolic acid. Still another patent 2,258,390 issued to W. D. Martin issued on Oct. 7, 1942 discloses the use of pine rosin in special formulations including kerosene for use as a larvacide.

OBJECTS OF THE INVENTION

It is an object of this invention to provide a composition and method which is economical, easy and safe to use, and which is effective in killing and controlling fire ants, and which is assimilable in the environment without any deleterious effects.

It is a further object of this invention to employ materials that have been present in the environment for long periods of time without any adverse effects whereby their saftey and acceptability to man and his environment is already established, thereby reducing or eliminating the need for long and expensive testing and documentation inorder to obtain government approval to employ the compositions and methods in commerce. These and other objects of the invention will become apparent by the disclosures made herein.

BRIEF DESCRIPTION OF THE INVENTION

These and other objects are accomplished by applicant's unexpected findings and invention that mixtures of terpene alcohols and terpene hydrocarbons such as pine oil in combination with surfactants kill fire ants when the mixture is contacted with mounds of fire ants, as more fully described and claimed hereinafter.

DETAILED DESCRIPTION OF THE INVENTION

In order that this invention may be more readily understood it will be described with respect to certain preferred embodiments, however it is to be understood that these embodiments are not to be construed as limiting the invention except as defined in the appended claims.

The preferred compositions of this invention are prepared by making a mixture of approximately one part of pine oil which is a mixture containing terpene alcohols and terpene hydrocarbons including alpha terpineol and alpha pinene with a quanity of a surfactant sufficient to form an emulsion, which is usually an amount equal to the pine oil employed. This composition is then diluted for use in the field by using at least about one ounce of it per gallon of water, and preferably about five to six ounces of said emulsion per gallon of water. More particularly, optium results in killing fire ants are obtained by employing an emulsion made from commercially available pine oil materials, such as Unipine 85 manufactured by Union Camp Corporation with commercially available dish washing detergents, such as Dawn manufactured by Proctor & Gamble Corporation. The diluted composition is thoroughly mixed then applied to the locus of the fire ant mounds by pouring, injecting into or spraying the mounds.

Table 1 gives the results obtained in testing over 60 fire ant mounds. Ten of the mounds were used as controls, five of which had nothing done to them and five of which had plain water, in like amounts to the compositions of this invention being tested, poured over them. In Table 1 the "Date" is given in months/day; the "Location" were all in the southern part of Texas; the "Condition" is the weather condition at the time of the test;
"Time" is given in 24 hour clock terms; the "Temp" is in Fahrenheit; "Product" is the material actually employed in the test; complete descriptions of the Products tested are given in the notes following the Table; "Mound Size" is measured in inches and the "Results" are given in percentage of kill of the fire ants, with the time required to get the percentage kill.

Table 2 gives the details on the commercial products available for controlling and killing fire ants.

Table 3 gives the composition ranges for individual components found in United States Domestic pine oils, which may be employed in accordance with this invention.

TABLE 1

TEST MONITORING LOG

| Date | Location | Condition | Time | Temp. | Product | Mound Size | Results |
|---|---|---|---|---|---|---|---|
| Part 1 | | | | | | | |
| 9/16 | Woodbranch Field | Hot/Clear | 14:30 | 90 | Raid | 12 × 5 | 75% kill 30 minutes<br>95% kill 1 hour |
| 9/16 | Woodbranch Field | Hot/Clear | 14:30 | 90 | Prod Five | 10 × 4 | 75% kill 20 minutes<br>95% kill 1 hour |
| 10/26 | Residential Lawn | Cloudy | 15:30 | 71 | Prod Five | 12 × 4 | 60% kill 20 minutes<br>100% kill 22 hours<br>increased solution to ¼ C. |
| 10/26 | Residential Lawn | Cloudy | 15:30 | 71 | Enforcer | multiple | negligible 20 minutes<br>negligible 22 hours |
| 10/26 | Residential Lawn | Cloudy | 15:30 | 71 | Raid | 9 × 4 | 75% kill 20 minutes<br>90% kill 22 hours |
| 10/26 | Residential Lawn | Cloudy | 15:30 | 71 | Prod Five | 10 × 3 | 75% kill 20 minutes<br>95% kill 2½ hours<br>100% kill 22 hours |
| 10/26 | Residential Lawn | Cloudy | 15:30 | 71 | Enforcer | 2' × 5" | No impact 2 hours<br>Mound abandoned 3 days |
| 10/28 | Residential Lawn | Cool/Rainy | 10:30 | 65 | Raid | 9 × 3 | 90% kill 30 minutes |
| 10/28 | Residential Lawn | Cool/Rainy | 10:30 | 65 | Prod Five | 9 × 3 | 100% kill 30 minutes |
| 10/28 | Residential Lawn | Cool/Rainy | 10:30 | 65 | Amdro | 10 × 4 | No impact 2 hours<br>Mound abandoned 2 days |
| 10/28 | Residential Lawn | Cool/Rainy | 10:30− | 65 | Rid-A-Bug | 12 × 4 | 75% kill 2 hours |
| Part 2 | | | | | | | |
| 4/24 | Woodbranch Field | P Cldy | 11:50 | 78 | P5/UD | 18 × 5 | 80% kill 20 minutes<br>100% kill 35 minutes |
| 4/24 | Woodbranch Field | P Cldy | 11:55 | 78 | P5/UP | 12 × 6 | 100% kill 20 minutes |
| 4/24 | Woodbranch Field | P Cldy | 12:00 | 78 | P5/AT | 14 × 5 | 10% kill 20 minutes<br>20% kill 40 minutes |
| 4/24 | Woodbranch Field | P Cldy | 12:08 | 78 | Raid | 10 × 7 | 15% kill 20 minutes<br>60% kill 40 minutes |
| 4/24 | Woodbranch | P Cldy | 12:15 | 78 | P5/UP | 10 × 9 | 100% kill 15 minutes |
| 4/26 | Residential B. Hill | Clear | 17:15 | 72 | P5/UP | 12 × 12 | 100% kill 15 minutes<br>kills grass |
| 4/26 | Residential B. Hill | Clear | 17:15 | 72 | P5/UP | 10 × 10 | 100% kill 18 minutes<br>kills grass |
| 4/26 | Residential M. Craven | Clear | 9:15 | 72 | P5/UP | 20 × 2 | 100% kill 10 minutes<br>browns grass |
| 4/26 | Residential M. Craven | Clear | 9:25 | 72 | P5/UP | 8 × 8 × 8 | 100% kill 15 minutes |
| 4/26 | Residential M. Craven | Clear | 17:30 | 74 | P5/At | 15 × 9 | 25% kill 20 minutes<br>30% kill 40 minutes |
| 4/26 | Residential D. Hennley | Clear | 16:15 | 73 | P5/UP | 16 × 20 | 90% kill 10 minutes<br>kills grass |
| 4/26 | Residential D. Hennley | Clear | 16:20 | 73 | P5/UD | 15 × 16 | 80% kill 20 minutes |
| Part 3 | | | | | | | |
| 10/4 | Residential W. Sublette | Cloudy | 14:40 | 70 | P5/PB/UP | 12 × 6 | 20% slow kill on surface<br>2 day duration |
| 10/4 | Residential W. Sublette | Cloudy | 14:50 | 70 | Peanut Butter only | 10 × 6 | Negligible kill |
| 10/4 | Residential W. Sublette | Cloudy | 15:05 | 70 | Surfactant & Water | 14 × 4 | None |
| 10/5 | Residential D. Hennley | Cloudy/Rain | 14:30 | 71 | P5/PB/UP | 14 × 5 | 25% slow kill on surface |
| 10/5 | Residential D. Hennley | Cloudy/Rain | 14:40 | 71 | Peanut Butter only | 10 × 3 | Negligible kill |
| 10/5 | Residential D. Hennley | Cloudy/Rain | 14:45 | 71 | Surfactant only | 12 × 3 | None, browns grass |
| 10/5 | April Vig | Cloudy/ | 15:05 | 71 | Water only | 9 × 2 | None |

TABLE 1-continued

TEST MONITORING LOG

| Date | Location | Condition | Time | Temp. | Product | Mound Size | Results |
|------|----------|-----------|------|-------|---------|------------|---------|
| 10/5 | cul-de-sac April Vig cul-de-sac | Rain Cloudy/ Rain | 15:10 | 71 | UP & Water | 11 × 3 | 80% kill in 20 minutes spotty kill pattern due to poor suspension |

NOTES
1. Product 5 as indicated on Part 1 of Table I was the initial mixture used to test the hypothesis and consisted of ⅛ cup Real-Pine (a commercially available disinfectant with a composition of 30% pine oil) and ⅛ cup surfactant (Dawn Dishwashing Detergent) mixed in 1 gallon of water. The solution was mixed and poured on the villages as a mound drench. Ingredients are as follows:

Real-Pine: Pine Oil                               30%
              Soap                                   11%
              Isopropanol                             9%
              Inert Ingredients                      50%
   Dawn:      Water                                  50%
              Magnesium Alkyl Sulfate                15%
              Magnesium Alkyl Ethoxylate Sulfate     15%
              Amoniam Alkyl Ethoxylate Sulfate        7%
              Ethenyl                                 7%
              Amin Oxide                              2%
              Amonium Chloride                        2%
              Amonium Zyline Sulfinate                2%
              Trace of Minor Ingredients 2. Raid as indicated on Part 1 of Table 1 is a commercially available consumer product which is a concentrated mound drench solution that must be added to water. Ingredients by label are:
   Active Ing:      Chlorpyrifos [0,0-Diethyl-0-(3,5,6-trichlor-2-pyridyl)phosphorothioate    2.00%
   Inert Ingredients:                                                                        98.00%

3. Enforcer is a commercially available consumer product in an aerosol form utilizing a injection tube to penetrate the mound. Its ingredients by label are:
   Active Ing:      Tetramethrin [1-Cyclohexene-1. 2-Dicarboximido) methyl 2. 2-Di-           0.200%
                    methyl-3-(2-methylpenyl) Cylopropanecarboxlate]
                    Cyano (3-Phenoxyphenyl) Methyl 4 chloro-alpha-(1-methylethyl)             0.400%
                    Benzeneacetate
                    Petroleum Distillate                                                      2.278%
   Inert Ingredients: 97.122%

4. Andro is a commercially available consumer product which is a solid bait. It is sprinkled on the mound in significant proportion to cover the mound area. Ingredients by label are:
   Active Ing:      Tetahydro-5,5-dimethyl-2 (1H)-phrinidinone (3-4[trifluoro-                 0.88%
                    methyl)phenyl]-1-(2-[4-(trifluoromethyl)
                    phenyl]-ethenyl)-2-propenylidene
   Inert Ingredients: 99.12%

5. Rid-A-Bug is also a commercial mound drench solution Its ingredients by label are:
   Active Ing:      Chlorpyrifos [(0.0-diethyl 0-(3,5,6-trichloro-2-pyridyl) phosphorthioate   0.50%
                    3,7-Dimethyl-6-octen-1-ol                                                  0.011%
                    3,7-Dimethyl-6-octedien-1-ol                                               0.002%
                    3,7-Dimethyl-6-octanol                                                     0.002%
                    Xylene lange aromatic solvent                                              0.28%
   Inert Ingredients:                                                                          99.205%

6. All commercial products were applied by following label directions at the same time applications of my product were made to other mounds in the exact same conditions.

7. After further testing components in Real-Pine, it was determined that pine oil was the active ingredient. Further experiments were carried out with chemically produced versions of natural pine oil. The "product" codes shown on Part 2 substitute the ⅛ cup Real-Pine for ⅛ cup measures of three other substances, P5/UD indicates Unitene DTR was substituted for Real-Pine. P5/UP is the designation for Unipine 85 substituted for Real-Pine, while P5/AT indicates ALpha Terpineol was the substitute. In all cases the substitute was exactly ⅛ cup of the chemical to ⅛ cup N—Butyl Acetate. While the substitutes showed varying degrees of results, the inclusion of N—Butyl Acetate neither enhanced or negated the kill ratio and was only for masking agent purposes.

8. The results utilizing UD, UP, and AT individually indicated those to be the active ingredient when mixed in water and applied to the mounds. Using surfactant alone, water alone, or the two in combination showed no effective kill.

9. The results clearly indicate that UD, UP, and AT individually combined with a surfactant and added to water offer superior performance over and above the commercial products tested. The UP solution is far and away the most effective of all combinations and clearly out performs by leagues other off-the-shelf products.

10. The composition of the products, or abreviations for products, embraced within this invention, that are given in Table 1 are as follows:
    Product 5 (P5) - ⅛ cup of Real-Pine; ⅛ cup of Dawn mixed in one gallon of water. (See page 4 of Table 1 for composition of Peal-Pine and Dawn).
    Unipine 85 (UP) - A pine oil manufactured by Union Camp Corporation - 87.8% terpene alcohols; 11.9% terpene hydrocarbons; 0.3% moisture. This combination meets U.S. Government specification LLL-P-400A Type 1.
    Unitene DTR(UD) - 5% terpene alcohols; 55% monocyclic hydrocarbons; 25% pine oils; 9% camphene; 6% alpha pinene; and 0.01% moisture.
    Pine Oil - crude and refined. (See Table 3 for composition ranges of domestic oine oil).
    Alpha Terpinol (AT).
    Alpha Pinene (AP).

11. The test results indicated on Table 1 Part 3 were to test various ingredients separately from each other as well as an additional compound utilizing a mixture of ordinary peanut butter and Unipine 85 as indicated by the "product" code P5/PB/UP. In summary, the use of water as the only treatment,

TABLE 1-continued

TEST MONITORING LOG

| Date | Location | Condition | Time | Temp. | Product | Mound Size | Results |
|------|----------|-----------|------|-------|---------|------------|---------| and the use of water and surfactant in combination all had negligible results and simply caused the mound to wash away and the ants built another village. However, with the combination once again proved to be very lethel.

Utilizing a similar technique, peanut butter by itself was applied to mounds with no effect. However, the addition of enough Unipine 85 to form a fairly liquid paste again caused a substantial kill. However, like Amdro, the solid bait must be ingested and it is very difficult to determine the effectiveness other than observing the dead ants on the mound surface.

It should be noted that the label on Amdro indicates this is a food chain killer wherein soldier ants carry the bait into the mound (inferring to the queen). It also indicates that it should take from one to four weeks to kill an appreciable number of soldiers and the queen. Further, the label indicates a visible reduction in mound activity should be observed in two to eight weeks. Accordingly, the mixture of peanut butter and Unipine 85 does kill in a faster time frame, at least on the surface, whereas Amdro will not kill as fast or as effectively as products of this invention. Further, when it rains, or the bait is moisturized, Amdro looses its effectiveness entirely.

TABLE 2

COMMERCIAL PRODUCTS WITH HIGHEST CONSUMER ACCEPTABILITY PROFILE

Product: Raid Fire Ant Killer
Manufacturer: Johnson & Johnson
Active Ing:
Chlorpyrifos [0,0-Diethyl-0-(3,5,6-trichlor-2-pyridyl)phosphorothioate                2.00%
Inert Ingredients:                         98.00%
EPA Reg No.                                4822-264
EPA Est No. 4822-WI-1
Form: Liquid
Product: Enforcer Fire Ant Killer
Manufacturer: C & J Chemical
Active Ing:
Tetramethrin [1-Cyclohexene-1. 2-Dicarboximido) methyl 2. 2-Dimethyl-3-(2-methylpropenyl) Cylopropanecarboxlate]     0.200%
Cyano (3-Phenoxyphenyl) Methyl 4 chloro-alpha-(1-methylethyl) Benezeneacetate        0.400%
Petroleum Distillate                       2.278%
Inert Ingredients:                         97.122%
EPA Reg No. 40849-13
EPA Est No. 10807-GA-1 49830-GA-1
Form: Aerosol
Product: Rid-A-Bug
Manufacturer: Kenco Chemical & Manufacturing Company
Active Ing:
Chlorpyrifos [(0.0-diethyl 0-(3,5,6-trichloro 2-pyridyl) phosphorothioate            0.50%
3,7-Dimethyl-6-octen-1-ol                  0.011%
3,7-Dimethyl-2-6-octedien-1-ol             0.002%
3,7-Dimethyl-6-octanol                     0.002%
Xylene lange aromatic solvent              0.28%
Inert Ingredients:                         99.205%
EPA Reg No. 8845-34
EPA Est No. 8845-FL-1
Form: Liquid
Product: Amdro Fire Ant Insecticide
Manufacturer: American Cyanamid Company
Active Ing:
Tetahydro-5,5-dimethyl-2 (1H)—phrinidinone (3-4[trifluoromethyl)phenyl]-1-(2-[4-(trifluoromethyl) phenyl]-ethenyl)-2-propenylidene       0.88%
Inert Ingredients:                         99.12%
EPA Reg No. 241-160
EPA Est No. 33596-IL-01
Form: Granule

TABLE 3

COMPOSITION RANGES FOR INDIVIDUAL COMPONENTS FOUND IN DOMESTIC PINE OILS

| | RANGE FOR ALL GRADES OF PINE OIL | |
|---|---|---|
| | % Min. | % Max. |
| BI & TRICYCLIC TERPENE HYDROCARBONS | | |
| Tricyclene | ND | 0.1 |
| Alpha-Pinene | ND | 2.0 |
| Camphene | ND | 1.0 |
| Beta-Pinene | ND | 0.3 |
| MONOCYCIIC TERPENE HYDROCARBONS | | |
| cis-p-Menthane | ND | T |
| trans-p-Menthane | ND | 1:1 |
| 3-p-Menthene | ND | 0.3 |
| 1-p-Menthene(Carvomenthene) | ND | 1.2 |
| 8-Menthene | ND | 0.1 |
| 4(8)-p-Menthene | ND | T |
| alpha-Phellandrene | ND | 0.6 |
| beta-Phellandrene | ND | 0.4 |
| alpha-Terpinene | T | 2.3 |
| gamma-Terpinene | ND | 3.1 |
| Dipentene (d,1-Limonene) | 0.1 | 10.0 |
| p-Cymene | 0.1 | 4.5 |
| Terpinolene | 0.8 | 14.6 |
| 2,4(8)-p-Menthadiene | ND | 1.7 |
| alpha-p-Dimethyl-styrene | ND | 0.5 |
| TERPENE ALCOHOLS | | |
| Dihydroterpineol | ND | 6.1 |
| Terpinene-1-ol (3-p-Menthen-1-ol) | T | 13.1 |
| alpha-Fenchol | 1.5 | 11.3 |
| Terpinene-4-ol (1-p-Menthen-4-ol) | 1.1 | 11.3 |
| beta-Terpineol (cis & trans) | 0.5 | 9.2 |
| Terpineol (alpha & gamma) | 34.9 | 76.7 |
| Isoborneol | 0.1 | 4.3 |
| l-Borneol | ND | 14.6 |
| 8-Cymenol | ND | 0.9 |
| pino-Carveol | ND | 0.4 |
| 1,8-Terpin (Terpin hydrate) | ND | 0.7 |
| MISCELLANEOUS TERPENES (Ethers & Ketones) | | |
| 1,4-Cineole | ND | 5.2 |
| 1,8-Cineole | ND | 4.2 |
| Fenchone | ND | 2.0 |
| Camphor | 0.4 | 8.3 |
| Estragole (Methyl Chavicol) | ND | 2.4 |
| cis-Anethole | ND | 6.2 |
| trans-Anethole | ND | 2.5 |
| Pinol | ND | 0.1 |
| UNKNOWNS | <0.1 | 0.4 |

ND — Not Detected
T — Trace

Amoung the active ingredients for killing or controlling fire ants that may be employed in accordance with my invention are specific components of pine oil. For example, I have found that alpha pinene may be used instead of the pine oil, also, the specific fractions of pine oil resulting from its distillation are effective fire ant killers including crude pine oil and refined pine oil. Alternatively synthetic pine oil may be substituted in whole or in part for the natural material. The foregoing materials may be substituted for or used as a partial replacements for each other, in the same manner as above described.

Various alcohols may be employed such as methyl alcohol to facilitate the formation of the emulsions in the preferred embobiment of my invention. The lower aliphatic alcohols such as ethyl, propyl, butyl and similar alcohols may be used in whole or in part with the preferred methly alcohol of this invention.

The surfactants that may be used are those which cause the emulsification of the pine oil mixture of this invention. For example ordinary soap may be used or even the household detergents used for laundry or dishes may be used. The preferred surfactants to employ in accordance with my invention are products having a composition or function similar to Dawn. The amount of surfactant used to make the emulsions of the pine oil water mixture is only that amount necessary to make the emulsions. For example, when using concentrations of pine oil at the lower end of the preferred range in one gallon of water smaller amounts of liquid surfactant may be employed than when using concentrations of pine oil at the higher end of the preferred range.

The concentrations of ingredients employed to make up the compositions of this invention may be varied widely. For example, I have found that although one part of pine oil to one part of surfactant is preferred that more or less of each may be employed and all that is required is an amount which is effective in emulsifying the mixture. Mixtures of only half the amount of pine oil to surfactant and mixtures of twice the amount of pine oil to alcohol are usefull. The amount of pine oil/surfactant emulsion employed in making the diluted composition for use in the field is preferably at least one ounce of said mixture to one gallon of water; the optimum being about two to three ounces of each to one gallon of water. Although concentrations as high as one to one to eight of active ingredient to surfactant to water may be employed in accordance with this invention, these higher concentrations are not necessary for effective kill, except under extreme conditions requiring faster kill. When using these high concentrations the surrounding environment may be deleteriously effected, for example, by browning of nearby vegetation. However, more may be used with the concommittent result that there is faster and more effective kill of the fire ants. By doubling the strength of active ingredient in accordance with this invention one may double the kill in half the time, and so on, however the effects on the environment and economical reasons are best served by using an effective amount which in accordance with this invention is between about 1 to 1 to 128 to between about 1 to 1 to 8 of pine oil/surfactant/water, respectively.

It is to be understood that various modifications within the spirit and scope of my invention are possible, some of which have been referred to above, and although I have given detailed description of my invention by illustrating specific embodiments, I do not intend to be limited thereto, except as defined by the following claims.

I claim:

1. A composition for controlling fire ants consisting of pine oil in amount effective in killing fire ants in combination with an emulsifying amount of a surfactant containing anionic and non-ionic surfactants including a dispersant and stabilizer, with water, said mixture of pine oil/surfactant/water being in the ratio of between about 1 to 1 to 128, to between 1 to 1 to 8, respectively.

2. A composition in accordance with claim 1 wherein a lower aliphatic alcohol is added to the mixture to facilitate emulsification.

3. A method for controlling fire ants which comprises applying a composition to the locus containing the fire ants, comprising pine oil, in an amount effective in killing fire ants, said composition containing an emulsifying amount of a surfactant and water.

4. A method for controlling fire ants in accordance with claim 3 wherein the mixture of pine oil and surfactant are present in about equal proportions.

5. A method for controlling fire ants in accordance with claim 4 wherein a lower aliphatic alcohol such as methyl alcohol is added to the pine oil to facilitate the emulsification.

6. A method for controlling fire ants in accordance with claim 4 wherein the pine oil/surfactant/water are in proportions between about 1 to 1 to 128 to between about 1 to 1 to 8, respectively.

* * * * *